(12) United States Patent
Bergmann (10) Patent No.: US 10,747,319 B2
(45) Date of Patent: Aug. 18, 2020

(54) APPARATUS AND METHODS FOR PROVIDING TACTILE SENSATION

(71) Applicant: OXFORD UNIVERSITY INNOVATION LIMITED, Oxford, Oxfordshire (GB)

(72) Inventor: Jeroen Henricus Maria Bergmann, Oxford (GB)

(73) Assignee: OXFORD UNIVERSITY INNOVATION LIMITED, Oxford, Oxfordshire (GB)

( * ) Notice: Subject to any disclaimer, the term of this patent is extended or adjusted under 35 U.S.C. 154(b) by 297 days.

(21) Appl. No.: 15/763,576

(22) PCT Filed: Sep. 27, 2016

(86) PCT No.: PCT/GB2016/053003
§ 371 (c)(1),
(2) Date: Mar. 27, 2018

(87) PCT Pub. No.: WO2017/055830
PCT Pub. Date: Apr. 6, 2017

(65) Prior Publication Data
US 2018/0284890 A1   Oct. 4, 2018

(30) Foreign Application Priority Data

Sep. 28, 2015   (GB) .................................. 1517114.3

(51) Int. Cl.
*G06F 3/01* (2006.01)
*A61F 2/68* (2006.01)
(Continued)

(52) U.S. Cl.
CPC ............... *G06F 3/016* (2013.01); *A61F 2/68* (2013.01); *A63F 13/245* (2014.09);
(Continued)

(58) Field of Classification Search
CPC .... G06F 1/163; G06F 2203/015; G06F 3/016; A61F 2002/5061; A61F 2/68;
(Continued)

(56) References Cited

U.S. PATENT DOCUMENTS

| 5,888,213 A | 3/1999 | Sears et al. |
| 6,100,874 A | 8/2000 | Schena et al. |

(Continued)

OTHER PUBLICATIONS

International Search Report and Written Opinion prepared by the European Patent Office dated Dec. 1, 2016, for International Application No. PCT/GB2016/053003.
(Continued)

*Primary Examiner* — Christine H Matthews
*Assistant Examiner* — Joshua Daryl D Lannu
(74) *Attorney, Agent, or Firm* — Jason H. Vick; Sheridan Ross, PC (57) ABSTRACT

Apparatus and methods for providing tactile sensation are provided. In one disclosed arrangement, there is provided a first magnet module comprising one or more magnetic elements. A mounting arrangement mounts the first magnet module to a human or animal body. A controller controls a tactile sensation applied by the first magnet module to the human or animal body by controlling a magnetic field applied to the first magnet module. The one or more magnetic elements are rotatably mounted and the controller controls the applied tactile sensation by rotating one or more of the magnetic elements using the applied magnetic field.

9 Claims, 7 Drawing Sheets

(51) Int. Cl.
*A63F 13/285* (2014.01)
*G06F 1/16* (2006.01)
*A63F 13/245* (2014.01)
*A61F 2/50* (2006.01)

(52) U.S. Cl.
CPC ............ *A63F 13/285* (2014.09); *G06F 1/163* (2013.01); *A61F 2002/5061* (2013.01); *A61F 2002/6827* (2013.01); *A61F 2002/6863* (2013.01); *G06F 2203/015* (2013.01)

(58) Field of Classification Search
CPC ...... A61F 2002/6863; A61F 2002/6827; A63F 13/285; A63F 13/245
See application file for complete search history.

(56) References Cited

U.S. PATENT DOCUMENTS

| | | | |
|---|---|---|---|
| 6,147,422 | A | 11/2000 | Delson et al. |
| 6,693,622 | B1 | 2/2004 | Shahoian et al. |
| 6,704,001 | B1 | 3/2004 | Schena et al. |
| 8,072,418 | B2 | 12/2011 | Crawford et al. |
| 8,766,784 | B2 * | 7/2014 | Radivojevic ......... G09B 21/003 340/407.1 |
| 2001/0026266 | A1 | 10/2001 | Schena et al. |
| 2002/0067336 | A1 | 6/2002 | Wegmuller et al. |
| 2004/0227727 | A1 | 11/2004 | Schena et al. |
| 2008/0200994 | A1 | 8/2008 | Colgate et al. |
| 2008/0297328 | A1 * | 12/2008 | Crawford ................ G08B 6/00 340/407.2 |
| 2009/0239652 | A1 | 9/2009 | Wang et al. |
| 2014/0253448 | A1 | 9/2014 | Nakamura et al. |
| 2015/0196454 | A1 * | 7/2015 | Levy ...................... A61H 19/32 600/38 |

OTHER PUBLICATIONS

Antfolk, Christian et al., "Sensory Feedback from a Prosthetic Hand Based on Air-Mediated Pressure from the Hand to the Forearm Skin" J Rehabil Med; 44: 702-707; 2012.
Schofield, Jonathon S. et al., "Applications of Sensory Feedback in Motorized Upper Extremity Prosthesis: A Review" Expert Rev. Med. Devices Early online, 1-13; 2014.
Schorr, Samuel B. et al., "Sensory Substitution via Cutaneous Skin Stretch Feedback" 2013 IEEE International Conference on Robotics and Automation (ICRA), Karlsruhe, Germany; May 6-10, 2013.
Weiss, Malte et al. "FingerFlux: Near-Surface Haptic Feedback on Tabletops" UIST'11, Santa Barbara, CA, USA; Oct. 16-19, 2011.
International Preliminary Report on Patentability for corresponding International Application No. PCT/GB2016/053003, dated Apr. 12, 2018.

* cited by examiner

APPARATUS AND METHODS FOR PROVIDING TACTILE SENSATION

CROSS REFERENCE TO RELATED APPLICATIONS

This application is a national stage application under 35 U.S.C. 371 of PCT Application No. PCT/GB2016/053003, having an international filing date of 27 Sep. 2016, which designated the United States, which PCT application claimed the benefit of Great Britain Patent Application No. 1517114.3 filed 28 Sep. 2015, the contents of each of which are incorporated herein by reference in their entirety.

The present invention relates to apparatus and methods for providing tactile sensation. The apparatus and methods may be used for example with prostheses, as well as in handheld control devices and tactile alert systems.

Systems for providing tactile sensation to a wearer of an artificial limb are known. The tactile sensation may provide feedback about a current state of the artificial limb and be referred to as tactile feedback. Currently, the most widely applied approach to tactile feedback is based on applying vibrations. This approach is referred to as vibrotactile feedback (VBF), and is implemented using small electric motors to provide the vibration. Difficulties with this method include that an electrical power source (e.g. a battery) is needed, the vibrations can affect socket movement, artefacts on the control signal can be introduced, and/or that separation of tissue from electrodes can occur. Approaches based on other technologies circumvent some of these issues, but most still require at least that an electrical power source is present. Systems that attempt to provide tactile stimulus without any electrical power source have so far involved an undesirably high threshold for the tactile stimulus (i.e. low sensitivity), as well as a relatively low spatial resolution.

Handheld control devices with tactile feedback are known, for example, in the context of computer gaming. However the range of tactile sensations that has so far been implemented is limited.

It is an object of the present invention to provide improved apparatus and methods for providing tactile sensation, which address, at least partially, one or more of the problems with the prior art.

According to an aspect of the invention, there is provided apparatus for providing tactile sensation, comprising: a first magnet module comprising one or more magnetic elements; a mounting arrangement configured to mount the first magnet module to a human or animal body; and a controller configured to control a tactile sensation applied by the first magnet module to the human or animal body by controlling a magnetic field applied to the first magnet module, wherein: the one or more magnetic elements of the first magnet module are rotatably mounted and the controller is configured to control the applied tactile sensation by rotating one or more of the magnetic elements using the applied magnetic field.

According to an aspect of the invention, there is provided apparatus for providing tactile sensation, comprising: a first magnet module comprising one or more magnetic elements; a mounting arrangement configured to mount the first magnet module to a human or animal body; a controller configured to control a tactile sensation applied by the first magnet module to the human or animal body by controlling a magnetic field applied to the first magnet module; and a prosthesis, wherein the controller is configured to control the magnetic field applied to the first magnet module dependent on at least one state of the prosthesis, thereby providing a tactile sensation indicative of the at least one state of the prosthesis.

Thus, arrangements are provided in which a magnetic field is used to control a tactile sensation imparted by a magnet module, for example by controlling a force distribution applied to one or more magnetic elements of the magnet module. This framework can be implemented simply and cheaply and can provide a wide range of tactile sensations reliably and reproducibly. The approach has been found to be particularly applicable to prostheses. Rotatably mounted magnetic elements have been found to provide particularly reliable and reproducible tactile sensations.

In an embodiment, the applied magnetic field is varied by changing a position and/or orientation of a second magnet module relative to the first magnet module. This mechanism can be implemented using a simple mechanical structure and does not require a separate electrical power source. For example, a change in the position or orientation of the second magnet module can be linked to a change in a state of a prosthesis (e.g. by movement of the prosthesis or a change in the relative positions of different components of the prosthesis, for example by articulation about joints of the prosthesis, such as bending of fingers, at elbows, at knees, etc.).

In an embodiment the tactile sensation is controlled in a continuously variable manner by applying a continuously variable control of a force distribution applied to the one or more magnetic elements of the first magnet module. This can be achieved in a practical and efficient way by providing a correspondingly continuously variable control of the magnetic field, for example by arranging for a second magnet module to be continuously movable (i.e. through a continuous range of positions and/or orientations) relative to the first magnet module. When applied to prostheses for example, providing a continuously variable range of tactile sensations enables more realistic and/or useful simulation of sensations that would be felt by the real limb that has been replaced, for example sensations associated with smooth movement of the prosthesis or with manipulation of an object using the prosthesis (e.g. grasping of objects having different compressibilities using a prosthetic hand).

In an embodiment, the first magnet module is adhered to the skin. Movement of the first magnet module stimulates sensation in the skin by stretching the skin. The stretching of the skin may occur as the first magnet module is tilted relative to the skin, driven into the skin (depressing the skin), or pulled away from the skin. The inventors have found this mechanism to be a particularly effective way of converting forces applied to the first magnet module to a sensation felt by the user.

In an alternative embodiment, the mounting arrangement holds the one or more magnetic elements of the first magnet module so as to apply a pressing force against the skin without adhesive. The pressing force is applied via direct or indirect contact between the magnetic element or magnetic elements and the skin. This allows larger relative movements or rotations of the magnetic elements relative to the skin in comparison with arrangements in which the magnetic elements are adhered to the skin.

In an embodiment, the first magnet module comprises a plurality of magnetic elements mounted so as to be spaced apart from each other. Optionally, the magnetic elements are positioned close enough together so that although the individual magnetic elements will apply tactile stimuli at different positions, the overall effect is sensed by a user as if it were originating from a single location. A tactile sensation that is more distinct than each of the individual stimuli in isolation is felt by the subject.

In an embodiment, the plurality of magnetic elements that are spaced apart from each other are also mounted so as to be rotatable about a common fixed axis of rotation. Common mounting apparatus can therefore be used for different magnetic elements, promoting ease of manufacture, low cost, and high compactness.

Embodiments can be implemented with or without an electrical power source. Embodiments which do not require an electrical power source are desirable because problems with increased bulk and/or longevity issues (e.g. batteries running flat) are avoided. Embodiments which do use an electrical power source can provide a wide range of variations in the magnetic field applied to the first magnet module, providing for example rapid and flexible changes in the tactile sensation provided. Very high sensitivity can also be achieved, for example detection of light touches to a prosthesis etc.

According to an alternative aspect, there is provided a control device having a gripping portion configured to be held in use by a user of the control device while moving a first component of the control device relative to a second component of the control device to provide a control signal, wherein the control device comprises: a first magnet module comprising one or more magnetic elements; and a controller configured to control a tactile sensation applied by the first magnet module to the user through the gripping portion by controlling a magnetic field applied to the first magnet module, wherein: the one or more magnetic elements of the first magnet module are rotatably mounted and the controller is configured to control the applied tactile sensation by rotating one or more of the magnetic elements using the applied magnetic field.

Thus, a new approach for providing tactile sensation in the context of control devices such as gaming controllers is provided. The range of tactile feedback that can be provided is therefore widened, providing improved variety and flexibility.

According to an alternative aspect, there is provided a method a method of providing tactile sensation, comprising: providing a first magnet module comprising one or more magnetic elements; controlling a tactile sensation applied by the first magnet module to a human or animal body to which the first magnet module is mounted by controlling a magnetic field applied to the first magnet module, wherein: the one or more magnetic elements of the first magnet module are rotatably mounted and the controlling of the tactile sensation comprises rotating one or more of the magnetic elements using the magnetic field.

According to an alternative aspect, there is provided a method of providing tactile sensation, comprising: providing a first magnet module comprising one or more magnetic elements; controlling a tactile sensation applied by the first magnet module to the human or animal body to which the first magnet module is mounted by controlling a magnetic field applied to the first magnet module, wherein: the one or more magnetic elements form part of a prosthesis and the control of the magnetic field is dependent on at least one state of the prosthesis, thereby providing a tactile sensation indicative of the at least one state of the prosthesis.

According to an alternative aspect, there is provided a method of providing tactile sensation to a user of a control device via a gripping portion of the control device while the user is holding the gripping portion, wherein: a first magnet module comprising one or more magnetic elements is provided and the method comprises controlling the tactile sensation applied by the first magnet module to the user through the gripping portion by controlling a magnetic field applied to the first magnet module, wherein: the one or more magnetic elements of the first magnet module are rotatably mounted and the controlling of the tactile sensation comprises rotating one or more of the magnetic elements using the magnetic field.

Embodiments of the invention will now be described, by way of example only, with reference to the accompanying drawings in which corresponding reference symbols indicate corresponding parts, and in which.

In an embodiment, examples of which are shown in FIGS. 1 to 15, there is provided an apparatus for providing a tactile sensation. In this context, a tactile sensation is understood to encompass any phenomenon that can be detected by nerves associated with the tactile sensory system of a human or animal. The tactile sensation may be imparted for example by pressing an object against skin or moving an object over the surface of skin (e.g. by rotating a cylindrically asymmetric object). Alternatively or additionally, the tactile sensation may be imparted by moving an object that is implanted underneath the skin.

The apparatus comprises a first magnet module 2. The first magnet module 2 may comprise a single magnetic element 3 or a plurality of magnetic elements 3. The magnetic elements 3 may each comprise a permanent magnet, for example a Neodymium magnet. FIGS. 1 to 3, 13 and 14 show example embodiments in which the first magnet module 2 comprises a single magnetic element. FIGS. 4, 5, 7 and 15 show example embodiments in which the first magnet module 2 comprises a plurality of magnetic elements 3. In any of these embodiments the plurality of magnetic elements 3 may be replaced by a single magnetic element 3 and vice versa.

Figure 13:
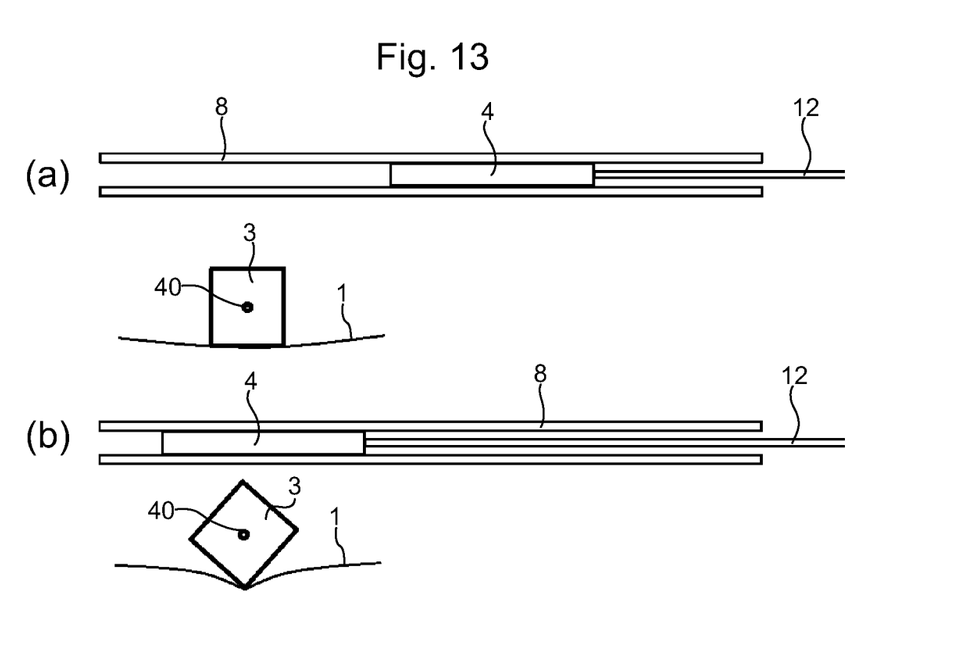
FIG. 13(a) is a schematic side sectional view of an apparatus for providing a tactile sensation in which a first magnet module comprises a rotatably mounted magnetic element and the second magnet module is configured to be movable parallel to the skin, the second magnet module being at a distal position at which substantially no magnetic force is applied to the first magnet module.
FIG. 13(b) is a schematic side sectional view of the apparatus of FIG. 13(a) in the case where the second magnet module has been moved into a proximal position adjacent to the first magnet module, thereby applying forces to the magnetic element which cause rotation of the magnetic element and impart a tactile sensation to the user.
Figure 14:
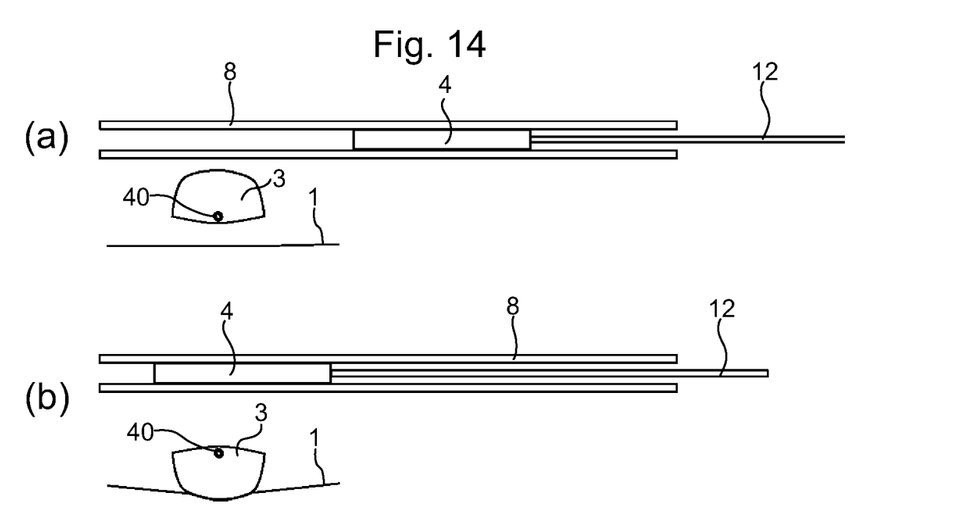
FIGS. 14(a)-(b) are the same as FIGS. 13(a)-(b) except that the rotatably mounted magnetic element has a different form.
Figure 15:
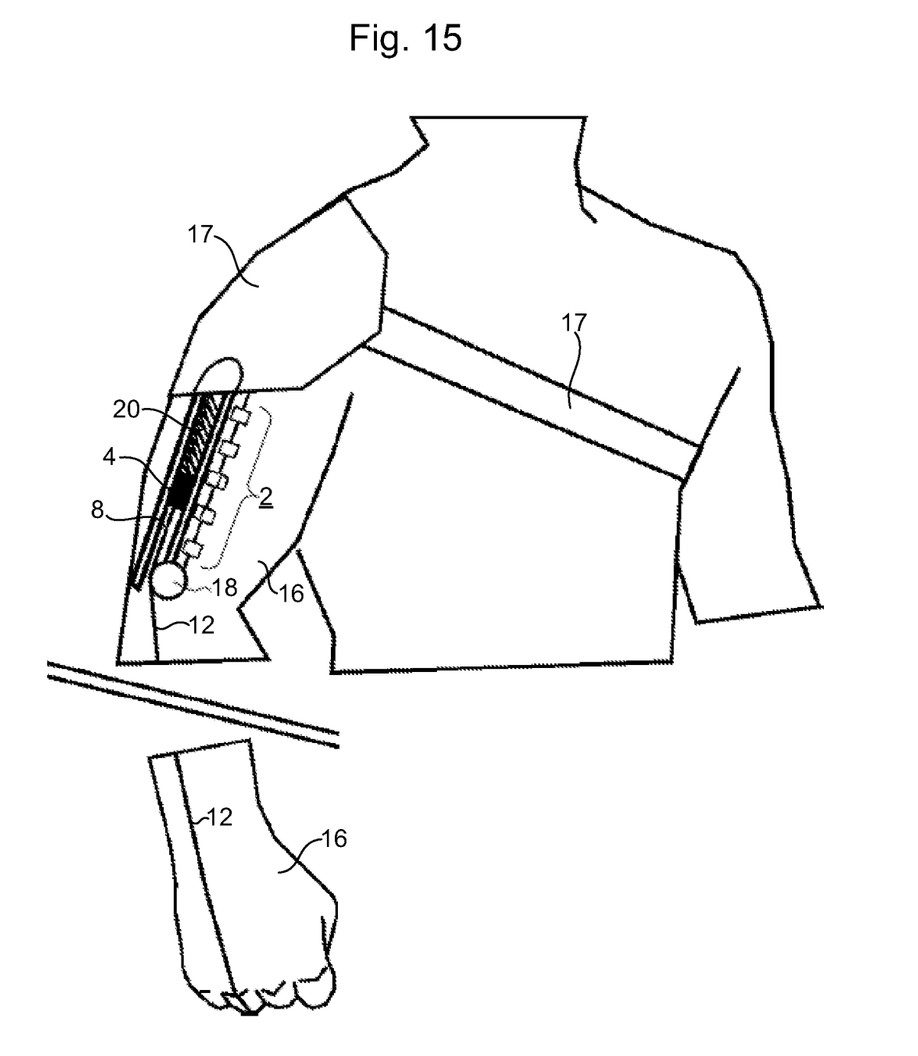
FIG. 15 depicts an implementation of the apparatus with a prosthetic arm, in the case where the apparatus comprises rotatably mounted magnetic elements.

A mounting arrangement 5 is provided for mounting the first magnet module 2 to the subject to which the tactile sensation is to be imparted. In embodiments the mounting arrangement comprises an adhesive for adhering one or more magnetic elements 3 of the first magnet module 2 to skin 1 of the subject. Skin-friendly adhesives are known in the art. In other embodiments the mounting arrangement 5 is configured to hold the first magnet module in close proximity to the skin without being adhered to the skin. In an embodiment, examples of which are shown in FIGS. 13-15, the mounting arrangement holds the one or more magnetic elements 3 of the first magnet module 2 so as to apply a pressing force against the skin without adhesive. The mounting arrangement 5 supports the first magnet module 2 in this case (i.e. where adhesive is not used) in such a way (e.g. by strapping or otherwise constraining the first magnet module to remain sufficiently close to the skin) that forces applied to the first magnet module 2 will result in tactile sensations being imparted to the subject (e.g. by causing one or more of magnetic elements 3 to press into the skin or otherwise deform the skin in a way which is dependent on the magnetic field applied to the magnetic elements 3). In other embodiments, the mounting arrangement 5 is adapted to allow the first magnet module 2 to be implanted underneath the skin, e.g. by encasing the first magnet module in a material that is tolerated underneath the skin. In the embodiments discussed below in which the first magnet module 2 is shown as adhered to the skin 1, it should be understood that this is not essential and that any other approach for mounting the first magnet module such that it can impart a tactile sensation to the subject could be used instead in any of these embodiments.

In embodiments, the mounting arrangement 5 and first magnet module 2 are configured such that a tactile sensation is imparted via stretching of the skin, which the inventors have found is particularly effective.

A controller 6 is provided to control the tactile sensation applied by the first magnet module 2. The tactile sensation is controlled by controlling a magnetic field applied to the first magnet module 2. Controlling the magnetic field controls a distribution of forces applied to the first magnet module 2 according to the laws of electromagnetism. The distribution of forces may cause a change in position or orientation of one or more of magnetic elements 3 forming the first magnet module 2, which when sufficiently large may be felt by the subject as a tactile sensation (e.g. due to skin stretching). The strength of the tactile sensation can be selected by appropriate selection of the magnetic strength of the one or more magnetic elements 3 forming the first magnet module 2. Increasing the magnetic strength of the one or more magnetic elements 3 will tend to increase the strength of the tactile sensation and decreasing the magnetic strength of the one or more magnetic elements 3 will tend to decrease the strength of the tactile sensation. The magnetic strength of the one or more magnetic elements 3 may be seen as a parameter that can be varied to optimise the tactile sensation to the particular application in question. For example, the magnetic strength of the one or more magnetic elements 3 may be changed to account for the likely amount and/or intensity of other signals or environmental factors (e.g. noise, etc.) which may distract the subject from the tactile sensation. Where such other signals or factors are likely to be very distracting it may be desirable to arrange for the tactile sensation to be stronger than otherwise, to ensure that the tactile sensation is noticed. Alternatively or additionally, the magnetic strength of the one or more magnetic elements 3 may be changed to account for attributes of the person wearing the system (e.g. elderly people, who may be less sensitive to tactile stimuli, may benefit from use of stronger magnetic elements 3 to provide a more easily discernible tactile sensation). Alternatively or additionally, the strength of the tactile feedback may be adjusted using other features. For example, the controller 6 may be adjustable to increase or decrease the strength of the magnetic field applied to the first magnet module 2 for a given tactile sensation to be imparted. For example, where the controller 6 is configured to control a position and/or orientation of a second magnet module (as discussed in further detail below), the magnetic strength of the second magnet module (e.g. of one or more magnetic elements, each comprising a permanent magnet, making up the second magnet module) may be adjusted (e.g. by replacing one or more of the magnetic elements with a magnetic element of different strength).

In an embodiment the controller 6 controls the tactile sensation in a continuously variable manner by applying a continuously variable control of the force distribution applied to the one or more magnetic elements 3. This can be achieved by controlling the magnetic field in a continuously variable manner (e.g. such that the magnetic field pattern changes smoothly over a continuous range of states).

In embodiments, examples of which are shown in FIGS. 1-9 and 13-15, the apparatus comprises a second magnet module 4. The second magnet module 4 may comprise one or a plurality of magnetic elements, for example permanent magnets. The controller 6 controls the magnetic field applied to the first magnet module 2 by controlling at least one of the position and orientation of the second magnet module 4 relative to the first magnet module 2 (where the second magnet module 4 comprises a plurality of magnetic elements, control of the position and/or orientation of each of the magnetic elements may be applied). For example, a relatively large magnetic field may be applied by moving the second magnet module 4 into a proximal position relatively close to the first magnet module 2 and the magnetic field may be reduced by moving the second magnet module 4 into a distal position relatively far from the first magnet module 2. A continuous range of intermediate magnetic fields can be achieved by moving the second magnet module 4 through a range of intermediate positions in between the proximal and distal positions.

In embodiments, movement of the second magnet module 4 relative to the first magnet module 2 is restricted to a range of predetermined trajectories. This may be achieved for example by using a guide 8 to guide movement of the second magnet module 4. The guide 8 may be fixedly mounted relative to the first magnet module 2 (i.e. so as to maintain a fixed spatial relationship therewith during use). Guiding movement of the second magnet module 4 ensures a predictable change in the force distribution applied to the first magnet module 2 and thereby a predictable change in the tactile sensation experienced by the user. In an embodiment, the guide 8 allows movement only backwards and forwards along a predetermined path. The predetermined path is chosen based on the needs of the particular application concerned, which may require a linear or curved path, or a combination of the two. In other embodiments the guide 8 is configured to allow more complex movements, including rotations within a predetermined plane or plurality of planes, or movements in various directions within a given pre-defined volume (e.g. cone, etc.).

Figures 1, 2:
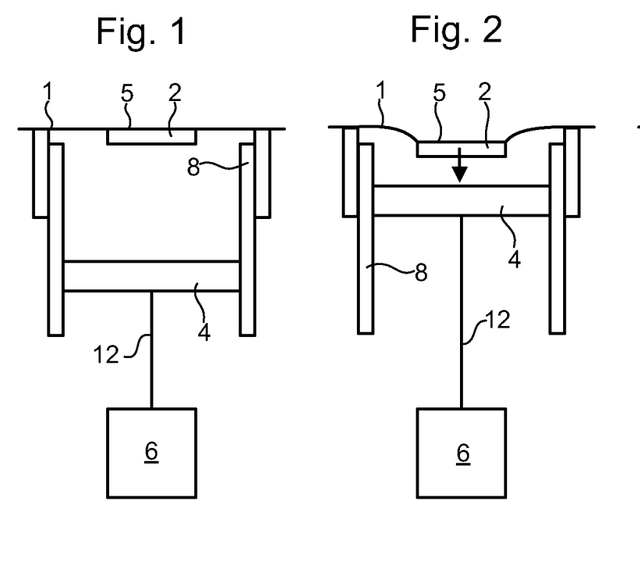
FIG. 1 is a schematic side sectional view of an apparatus for providing a tactile sensation comprising first and second magnet modules, the second magnet module being in a distal position at which substantially no magnetic force is applied to the first magnet module.
FIG. 2 is a schematic side sectional view of the apparatus of FIG. 1 in which the second magnet module has been moved closer to the first magnet module, to a proximal position, and an attractive force acts between them, thereby pulling skin towards the second magnet module and imparting a tactile sensation.
Figure 3:
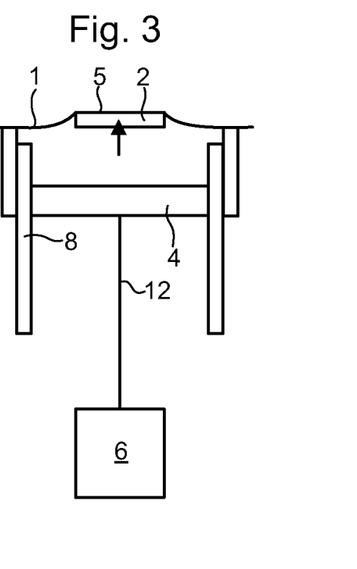
FIG. 3 is a schematic side sectional view of an alternative configuration to that of FIG. 2 in which the force acting between the first and second magnet modules is repulsive.

FIGS. 1-3 show example arrangements in which a guide 8 restricts movement of the second magnet module 4 to be linear in a direction perpendicular to the skin 1 of a subject. A coupling member 12 is provided for allowing the controller 6 to control movement of the second magnet module 4 within the guide 8. In an embodiment of this type the guide 8 and second magnet module 4 may be cylindrical for example. The coupling member 12 may take various forms. The coupling member 12 may be a wire, rod or other device configured to transmit tensile and/or compressive forces, for example. Such an arrangement may be particularly appropriate where the controller 6 operates purely mechanically (without any electrical power source). In other embodiments, the coupling member 12 may be an electrical connection to drive a motor (not shown) that moves the second magnet module 4. In an embodiment the coupling member 12 is capable of applying a tensile force (i.e. pulling) only. In such an embodiment, and in other embodiments, a resilient member (not shown in FIGS. 1-3) may additionally be provided to oppose the tensile force (thereby biasing the second magnet module 4 towards the skin 1). For example, in the depicted orientation of FIGS. 1-3, a spring (not shown) may be provided for providing an upward force to the second magnet module 4 opposing the pulling force from the coupling member 12.

In FIG. 1 the controller 6 holds the second magnet module 4 in a distal position which exerts substantially no force on the first magnet module 2. A tactile sensation imparted by the first magnet module 2 is therefore minimal or non-existent in this state. In FIGS. 2 and 3 the controller 6 has moved the second magnet module 4 into a proximal position which is relatively close to the first magnet module 2. The magnetic field of the second magnet module 4 applies a significant magnetic force to the first magnet module 2. In the example of FIG. 2 the force is attractive and the first magnet module 2 is pulled towards the second magnet module 4, causing a stretching outwards of the skin. In the example of FIG. 3 the force is repulsive and the first magnet module 2 is pushed away from the second magnet module 4, causing a pressing inwards of the skin. Both arrangements (FIGS. 2 and 3) cause stretching of the skin, and/or compression or expansion of tissue beneath the skin, which is felt as a tactile sensation by the subject. The tactile sensation varies continuously, gradually weakening, as the second magnet member 4 is pulled progressively further away from the proximal position illustrated in FIGS. 2 and 3. A continuously variable control of the tactile sensation is thereby achieved.

Figure 4:
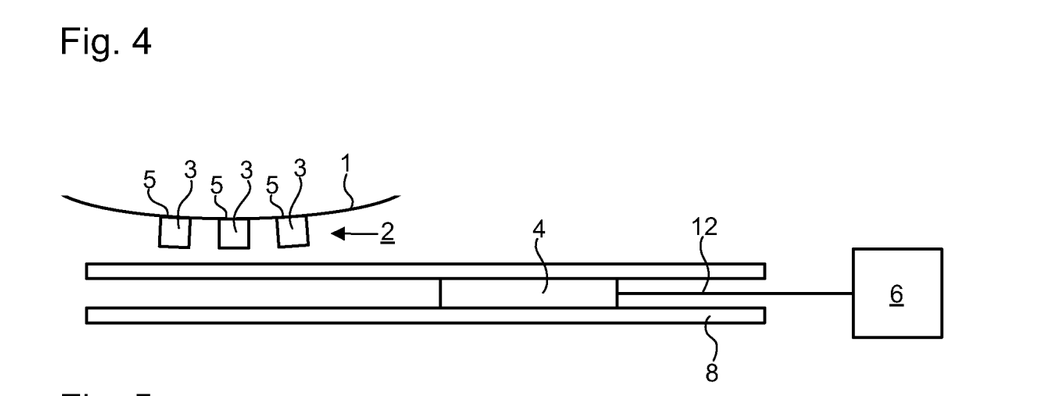
FIG. 4 is a schematic side sectional view of an alternative apparatus for providing a tactile sensation in which a first magnet module comprises a plurality of magnetic elements and the second magnet module is configured to be movable parallel to the skin, the second magnet module being at a distal position at which substantially no magnetic force is applied to the first magnet module.
Figure 5:
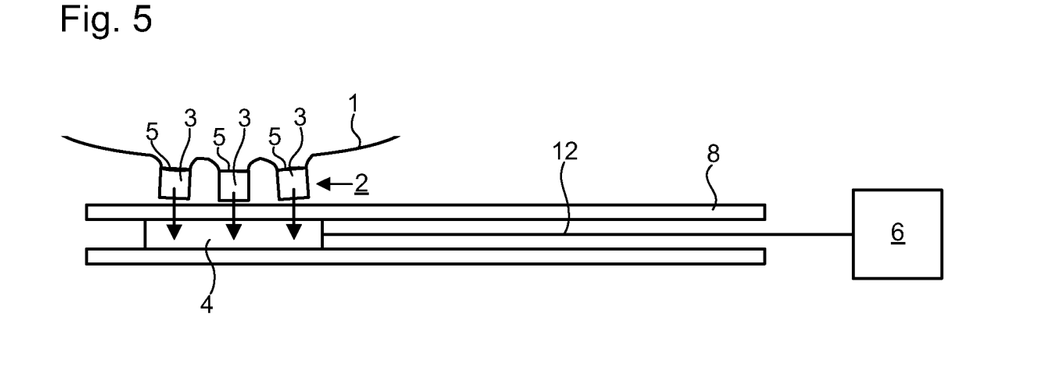
FIG. 5 is a schematic side sectional view of the apparatus of FIG. 4 in the case where the second magnet module has been moved into a proximal position adjacent to the first magnet module, thereby applying forces to the magnetic elements which are detected as a tactile sensation by the user.

FIGS. 4, 5, 13 and 14 depict alternative embodiments in which a guide 8 guides movement of the second magnet module 4 in a direction substantially parallel to the skin 1 (instead of perpendicular to the skin 1). The apparatus may protrude less in the direction perpendicular to the skin 1 than arrangements of the type shown in FIGS. 1-3. FIGS. 4, 13(*a*) and 14(*a*) show the apparatus in a state where the second magnet module 4 is in a distal position exerting substantially no force on the first magnet module 2. FIGS. 5, 13(*b*) and 14(*b*) depict the apparatus in a state in which the second magnet module 4 is at a proximal position directly opposite the first magnet module 2 and providing a maximal (e.g. attractive) force to the first magnet module 2. In other embodiments, a repulsive force may be applied or a combination of repulsive and attractive forces may be applied (e.g. a repulsive force may be applied to one or more of a plurality of magnetic elements 3 of the first magnet module 2 while an attractive force is applied to one or more other ones of the plurality of magnetic elements 3 which have their polarities orientated differently).

In the arrangements of FIGS. 1-3, the first magnet module 2 comprises a single magnetic element that simply moves towards and away from the second magnet module 4. In other embodiments more complex manipulation of the first magnet module 2 may be achieved. For example, in the arrangement of FIGS. 4 and 5 the first magnet module comprises a plurality of magnetic elements 3 which can each experience different magnetic forces and thereby apply different tactile sensations to the skin 1. Furthermore, the movement of the second magnet module 4 parallel to the skin 1 causes tilting of the magnetic elements 3 (i.e. rotation about an axis parallel to the skin 1), rather than a simple pushing inwards or pulling outwards, for intermediate positions of the second magnet module 4 (i.e. positions other than where the second magnet module 4 is directly beneath the magnetic elements 3 of the first magnet module 2). An amount of the tilting may vary between different ones of the magnetic elements 3. By varying the number of magnetic elements 3 and the trajectory of the second magnet module 4 it is possible to achieve a wide range of different tactile sensations.

Figure 6:
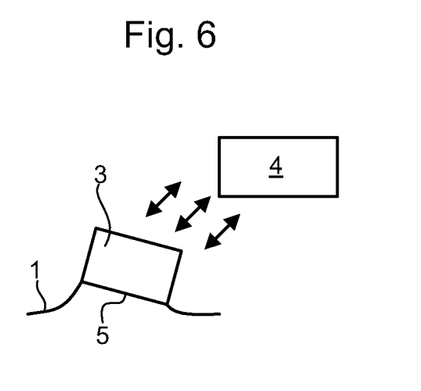
FIG. 6 is a schematic side sectional view showing how a magnetic element of the first magnet module may tilt in response to proximity of the second magnet module, thereby applying a tactile sensation via asymmetric stretching of the skin.

FIG. 6 depicts in more detail how tilting of a magnetic element 3 can cause stretching of the skin 1 in an asymmetric manner. The skin 1 is stretched more on one side of the magnetic element 3 than on the other side of the magnetic element 3. The inventors have found that such asymmetric stretching is a particularly effective way of imparting a tactile sensation.

FIGS. 13 and 14 depict embodiments in which a magnetic element 3 of the first magnet module 2 is rotatably mounted. In the embodiments shown only a single rotatably mounted magnetic element 3 is shown but it will be understood that plural rotatably mounted magnet elements 3 could be provided. The controller 6 controls the applied tactile sensation in each case by rotating the magnetic element 3 (or magnetic elements) using the applied magnetic field. In the examples of FIGS. 13 and 14, the applied magnetic field is varied by moving the second magnet module 4. The magnetic element 3 in each case is cylindrically asymmetric about an axis 40 of the rotation. As the magnetic element 3 is made to rotate, the cylindrical asymmetry means that a tactile sensation applied by the magnetic element 3 varies as a function of the angle of rotation. In the arrangement of FIG. 13, for example, it can be seen that the rotational position in FIG. 13(*a*) is such as to impart a relatively low tactile sensation (due to a flat portion being pressed against the skin 1), whereas the rotational position in FIG. 13(*b*) is such as to impart a higher tactile sensation (due to a corner portion being pressed against the skin 1). In the arrangement of FIG. 14, the rotational position of FIG. 14(*a*) is such that no tactile sensation is imparted (due to the magnetic element being separated from the skin 1), whereas the rotational position in FIG. 14(*b*) is such as to impart a higher tactile sensation (due to the magnetic element being brought into contact with the skin 1).

In an embodiment, the axis of rotation 40 of each of the one or more magnetic elements 3 that are rotatably mounted is a fixed axis of rotation 40 relative to the mounting arrangement. This is the case in the examples of FIGS. 13-15.

Figure 16:
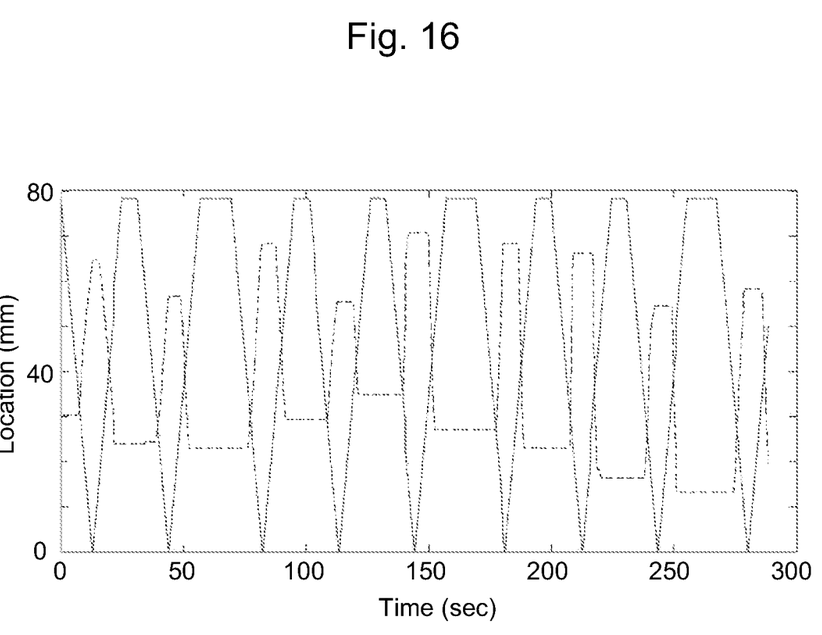
FIG. 16 is graph of experimental data showing responses of a user to tactile stimuli provided by the apparatus.

It has been found that rotation of a magnetic element 3 is a particularly efficient way of transmitting a tactile sensation. FIG. 16 is a graph of experimental data showing responses of a user to tactile stimuli provided by an apparatus comprising rotatably mounted magnetic elements 3 mounted to the user. The vertical axis represents location in mm. The horizontal axis represents time in seconds. The solid line shows the variation of location with time of the second magnet module 4 (which drives rotation of a magnetic element 3 of the first magnet module 2). The user was asked to move a computer mouse sideways every time the user felt a tactile sensation applied by the apparatus. It can be seen from the graph that there is very clear and reliably correlation between the application of the tactile sensation and a recognition of the tactile sensation by the user.

Figure 7:
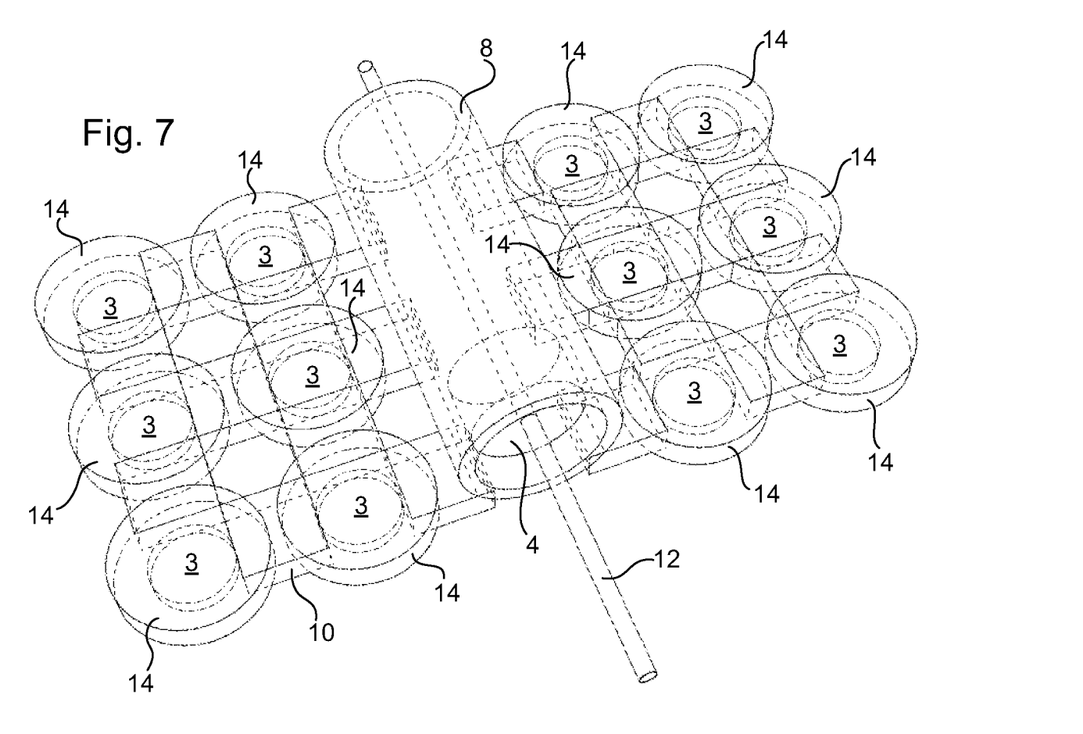
FIG. 7 is a schematic perspective view of an example first magnet module comprising a plurality of magnetic elements, a guide and a second magnet module configured to move within the guide.
Figure 8:
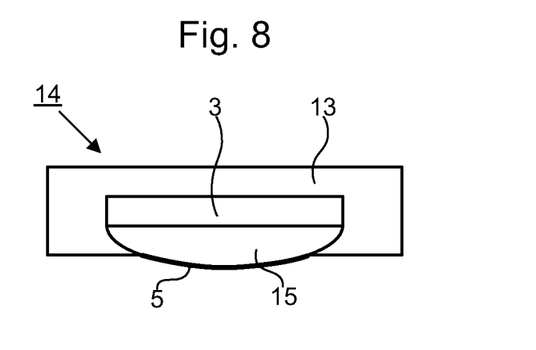
FIG. 8 is a schematic side sectional view of a housing for a magnetic element of the first magnet module.

FIG. 7 shows a detailed example configuration in which a first magnet module having a plurality of magnetic elements 3 is used. In this example each of the magnetic elements 3 is mounted within a housing 14. An example configuration for the housing 14 is shown in FIG. 8. The housing 14 comprises an encapsulation layer 13, formed for example from silicone. Silicone has various desirable properties, including being non-volatile, resistant to high temperatures, resistant to humidity, and resistant to ozone and UV degradation. The inventors have found that it is difficult however to provide a reliable bond between silicone and skin 1 using standard skin-friendly adhesives. In this embodiment, this challenge is addressed by providing an adhesion promoting body 15 attached to the magnetic element 3 on one side and presenting a surface for adhesion to skin 1 (using a skin friendly adhesive 5) on the other side. Various materials which may be adhered more readily to skin than silicone may be used for the adhesion promoting body 15. In one embodiment the adhesion promoting body is formed from a thermoplastic polymer or adhesive. The encapsulation layer 13 and adhesion promoting body 15 are configured so that the magnetic element 3 is sealed from the outside environment.

The magnetic elements 3 are connected together so as to remain spaced apart from each other in use. In the particular example shown the magnetic elements 3 form a rectangular planar grid, but other arrangements are possible. The inventors have found that providing individual magnetic elements 3 spaced out in this manner provides a more effective way of achieving a tactile sensation than is readily possible using a single magnetic element 3. In an embodiment, the magnetic elements 3 are arranged so that the tactile sensation experienced by a user feels as if it is originating from a single location, even though the tactile sensation is formed by a plurality of individual interactions with the skin 1. This effect may be referred to as tactile funneling. The guide 8 in this example is cylindrical and lies in between two distinct sets of magnetic elements 3 (a group of six on each side). The second magnet module 4 is moveable longitudinally within the guide 8. The movement is controlled with coupling member 12. The force provided between the second magnet module 4 and each of the magnetic elements 3 will result in a tilting deformation of each of the magnetic elements 3 in the manner depicted in FIG. 6, causing a tactile sensation to be imparted to the subject.

In embodiments, the apparatus for providing a tactile sensation is applied to a prosthesis. In examples of such embodiments, the controller 6 controls the magnetic field applied to the first magnet module 2 dependent on at least one state of the prosthesis, thereby providing a tactile sensation indicative of the at least one state of the prosthesis. Where a second magnet module 4 is provided, the second magnet module 4 may be coupled to the prosthesis such that at least one of the position and orientation of the second magnet module 4 relative to the first magnet module 2 is dependent on at least one state of the prosthesis.

In an embodiment the prosthesis comprises a prosthetic limb comprising a first component and a second component, wherein one or more of the following is changeable: a position of the first component relative to the second component, an orientation of the first component relative to the second component, and a shape of the first component. The at least one state of the prosthesis comprises one or more of the following: the position of the first component relative to the second component, the orientation of the first component relative to the second component, and the shape of the first component. In an embodiment, the first component is a moveable prosthetic limb such as a finger, thumb, lower leg, upper leg, forearm, upper arm, etc. The second component may be any other limb (prosthetic or natural). The first component may be a finger and the second component may be another finger or another part of the forearm, for example. The first component may be a lower part of the leg and the second component may be another part of the leg. The first component may be a forearm and the second component may be an upper part of the arm. Various other combinations of first and second components are possible.

Figure 9:
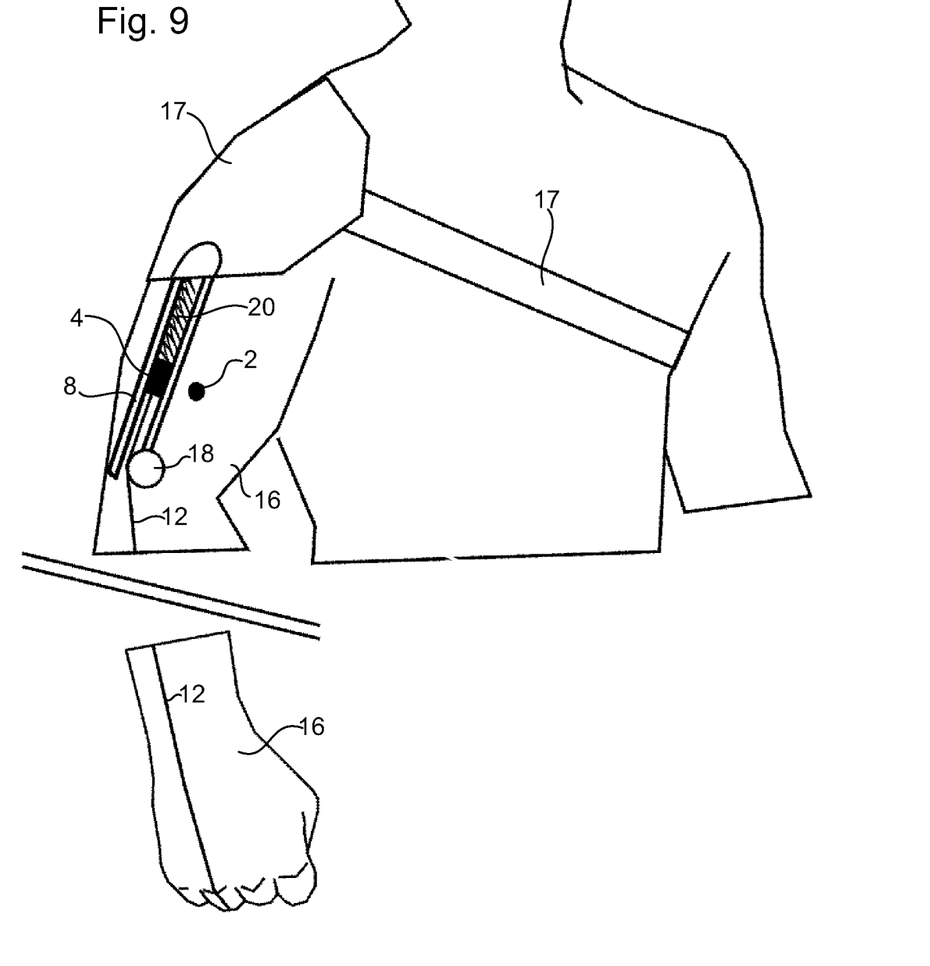
FIG. 9 depicts implementation of the apparatus with a prosthetic arm.

FIGS. 9 and 15 depict example arrangements. In these example the prosthesis 16 comprises a prosthetic limb (comprising a portion of an arm and a hand). The first component may be an actuatable portion of the prosthetic hand, for example one or more actuatable prosthetic fingers, or the hand itself (which may be actuatable in the sense of being movable about the wrist). The second component may be any other portion of the prosthesis serving as a suitable reference. A change in state of the first component (e.g. bending of the finger, flexing of the wrist, etc.) causes a corresponding change in the position of the second magnet module 4 (e.g. by pulling on a mechanical coupling member 12 connected to the second magnet module 4) and a corresponding change in a tactile sensation felt by the user. In the case of FIG. 9, the first magnet module 2 is shown as a single localised element, comprising for example a single magnetic element. In the case of FIG. 15, the first magnet module 2 comprises a plurality of magnetic elements. The plurality of magnetic elements are rotatably mounted so as to be rotatable about a common fixed axis of rotation. Movement of the second magnet module 4 can be used to cause different ones of the magnetic elements to rotate and thereby impart a variety of different and/or progressive tactile sensations to the user. One or more of the magnetic elements may be cylindrically asymmetric about the axis of rotation. The magnetic elements may each have the same shape and/or size or may have different sizes and/or shapes.

Alternatively or additionally, the at least one state of the prosthesis 16 may comprise a size and/or spatial distribution of a pressure applied to the prosthesis (e.g. to an external surface of the prosthesis). The tactile sensation can therefore provide information about objects that the prosthesis 16 is manipulating (e.g. holding) or touching (e.g. brushing against).

The continuously variable control provided by embodiments of the invention may be particularly valuable in the context of prostheses 16. The continuously variable control may be used for example to provide information about a continuously varying change in the state of the prosthesis 16. For example, a continuously changing position of a component of the prosthesis 16 (e.g. a finger or angle of a forearm) can be conveyed to the subject. This provides more natural imitation of sensations provided by real limbs. Alternatively or additionally, a pressure applied to the prosthesis 16 may be detected in a continuously variable manner. For example, if the user pushes a portion of the prosthesis 16 against an object, the way in which the pressure applied to the prosthesis 16 changes as the object is deformed by the pressure can be conveyed accurately to the user as a continuously changing tactile sensation. This allows a user to detect for example the difference between holding a spongy object and holding a hard undeformable object.

In the examples of FIGS. 9 and 15, the second magnet module 4 moves within a guide 8 attached substantially parallel to the skin 1 of the upper arm. The guide 8 is held in place by a sheath and belt 17 worn by the subject. The coupling member 12 comprises a wire passed over a guiding roller 18. The wire provides a tensile mechanical connection between a first component located at the hand of the prosthesis 16 and the second magnet module 4. A spring 20 provides a force on the second magnet module 4 opposite to the tensile force applied by the coupling member 12. Actuation of the first component at the hand causes the coupling member 12 to pull on the second magnet module 4, thereby changing the position of the second magnet module 4 relative to the first magnet module 2, which is sensed as a tactile sensation by the user (e.g. due to stretching of the skin imparted by movement of the first magnet module 2 or a pressing against the skin in different ways caused by rotation of the magnetic elements of the first magnet module 2).

Figure 10:
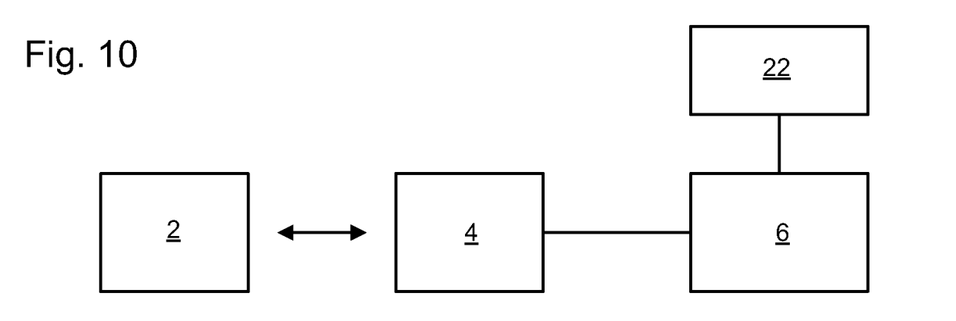
FIG. 10 depicts components of an apparatus for providing a tactile sensation comprising an electrical power source.

As mentioned above, the controller 6 may control the magnetic field applied to the first magnet module 2 using an electrical power source instead of or in addition to using a mechanical mechanism. FIG. 10 is a schematic depiction of such an arrangement. The controller 6 is shown as being connected to an electrical power source 22 (this may be separate from the controller or may form part of the controller). Using this electrical power source 22 the controller 6 controls the magnetic field applied to the first magnet module 2. This may be achieved by driving movement of a second magnet module 4, for example using an electrical motor. Alternatively or additionally, the controller 6 may generate a magnetic field directly, for example by driving a current through a coil (an electromagnet). In an embodiment of this type the second magnet module 4 may not be required.

Figure 11:
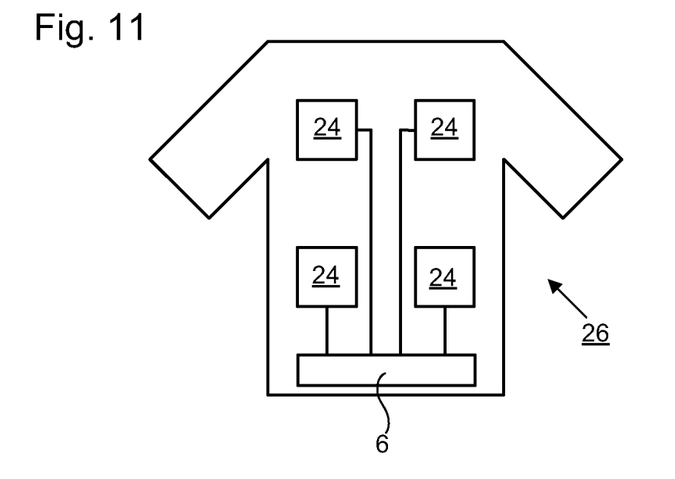
FIG. 11 depicts a tactile alert element configured to be worn by a user.

In other embodiments, the apparatus for providing a tactile sensation is applied to a tactile alert element. An example of such an arrangement is shown in FIG. 11. The tactile alert element 26 is configured to be worn by a subject, for example as a garment or article of clothing or attached to a garment or article of clothing, or otherwise worn by the subject (e.g. in the manner of a watch, waist-band, etc.) or attached to the subject (e.g. by adhering to the skin). The tactile alert element 26 provides a tactile sensation to the subject via one or more sensation imparting units 24. Each of the sensation imparting units 24 comprises a first magnet module 2 comprising one or more magnetic elements 3 and the controller 6 controls a tactile sensation provided by the sensation imparting unit 24 by controlling a magnetic field applied to the first magnet module 2 (e.g. using movement of a second magnet module 4). The one or more magnetic elements 3 of the first magnet module 2 may be rotatably mounted and the controller 6 may control the applied tactile sensation by rotating one or more of the magnetic elements 3 using the applied magnetic field.

The controller 6 communicates with the sensation imparting units 24 in order to provide the tactile sensation required. The controller 6 may comprise communication hardware to allow communication with devices wishing to convey information to the user via the sensation imparting units 24. For example, the tactile alert element 26 may be worn by an operator of a piece of equipment (e.g. by a pilot of a plane or a driver of a car or truck). The tactile alert element 26 may be configured to provide a tactile sensation to the user that is indicative of a change in state of the equipment which he or she is operating. The change in state may be such as to require emergency action to be initiated by the user. The tactile sensation may therefore provide a warning to a user. Alternatively or additionally, the tactile sensation may be configured to provide navigational information to a user. The navigational information may guide a user navigating to a particular desired location for example and/or provide information about imminent navigational actions required by a user (e.g. due to the approach of a stop signal or a turning in a road or path). The provision of multiple sensation imparting units 24 provides safety (because if the user happens not to detect the tactile sensation provided by one unit 24 he or she may nevertheless detect the tactile sensation imparted by another unit 24). Alternatively or additionally, by providing different tactile sensations at different sensation imparting units 24 it is possible to convey more complex information to the user than is possible using only a single unit 24. Providing tactile sensations rather than visual or audio indications may interfere less with the user's normal functioning, enabling the user to continue to operate efficiently while receiving the tactile information, even in the case where an emergency situation has arisen. For example in the context of the driver of a car, he or she will not be distracted by visual alerts when trying to keep his or her eyes on the road.

Figure 12:
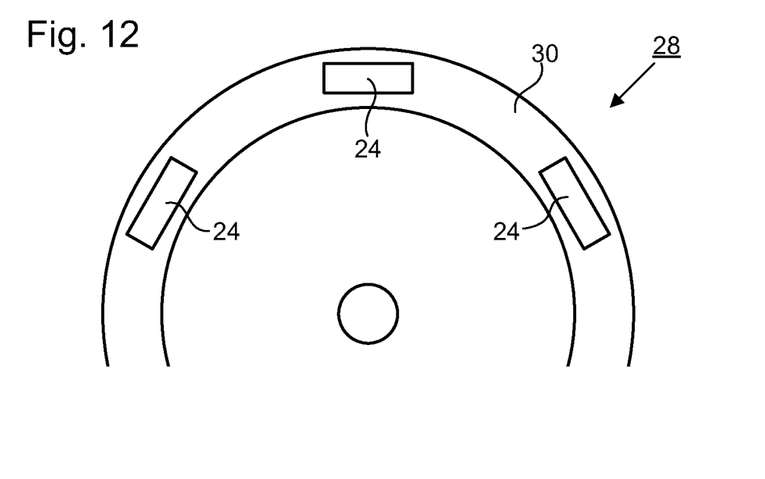
FIG. 12 depicts a control device having a gripping portion configured to be held in use by a user of the control device.

In other embodiments, the apparatus for providing a tactile sensation is used in a control device 28 having a gripping portion 30 to be held by a user. An example of such an arrangement is shown in FIG. 12. In this embodiment, the control device 28 is a steering wheel for a vehicle or a computer game. The user moves a first component of the control device 28 (e.g. the wheel in the example of FIG. 12) relative to a second component (e.g. a base unit, not shown) to provide a control signal (e.g. indicating the extent to which the wheel has been turned in the example of FIG. 12). In other control devices, the first component may comprise a joystick or similar. The gripping portion 30 is provided with one or more sensation imparting units 24 which may be configured as discussed above in relation to the embodiment of FIG. 11 for example. In the context of control devices for gaming, the tactile sensation can be used to provide a more immersive "virtual reality" experience. The provision of tactile sensations can provide a more immersive experience by creating touch sensations that are linked with the game environment. The flexibility of the apparatus disclosed herein makes it possible to provide tactile sensations that make interactions in the virtual world seem more realistic. For example the tactile sensation can be used to simulate touching and handling of objects realistically. In the context of gaming, interactions with other players (e.g. touching or bumping into other players) can be simulated. In the context of surgical operations in medicine, interactions between a robot being used to operate on a patient and the anatomy of the patient can be simulating realistically (e.g. contact or deformation of tissue can be fed back to the surgeon as corresponding tactile sensations).

References to magnetic elements in the above description and in the claims is understood to encompass both permanent magnets and magnets which operate as electromagnets by being driven by an electrical power source. Any one or more of the magnetic elements may also be implemented using one or more encapsulated ferrofluids.

Any of the features disclosed above may be combined in any combination.

Further embodiments are provided in below numbered clauses:

1. Apparatus for providing tactile sensation, comprising:
   a first magnet module comprising one or more magnetic elements;
   a mounting arrangement configured to mount the first magnet module to a human or animal body; and
   a controller configured to control a tactile sensation applied by the first magnet module to the human or animal body by controlling a magnetic field applied to the first magnet module.

2. The apparatus of clause 1, wherein the mounting arrangement comprises an adhesive for adhering the first magnet module to skin.

3. A control device having a gripping portion configured to be held in use by a user of the control device while moving a first component of the control device relative to a second component of the control device to provide a control signal, wherein the control device comprises:
   a first magnet module comprising one or more magnetic elements; and
   a controller configured to control a tactile sensation applied by the first magnet module to the user through the gripping portion by controlling a magnetic field applied to the first magnet module.

4. The apparatus or device of any preceding clause, wherein the controller is configured to control the tactile sensation in a continuously variable manner by applying a continuously variable control of a force distribution applied to the one or more magnetic elements.

5. The apparatus or device of any preceding clause, wherein the first magnet module comprises a plurality of magnetic elements mounted spaced apart from each other.

6. The apparatus or device of any preceding clause, wherein the apparatus or device comprises a second magnet module and the controller is configured to control the magnetic field applied to the first magnet module by controlling at least one of the position and orientation of the second magnet module relative to the first magnet module.

7. The apparatus or device of clause 6, wherein the apparatus or device comprises a guide for guiding movement of the second magnet module relative to the first magnet module.

8. The apparatus or device of clause 7, wherein the guide is fixedly mounted relative to the first magnet module.

9. The apparatus or device of clause 8, wherein:
   the guide allows movement of the first magnet module between a distal position and a proximal position;
   the distal position is a position at which a magnetic interaction between the first magnet module and the second magnet module is too weak to cause a tactile sensation; and
   the proximal position is a position at which the magnetic interaction between the first magnet module and the second magnet module is strong enough to cause a tactile sensation.

10. The apparatus or device of any preceding clause, wherein the magnetic field applied by the controller is at least partially generated using an electrical power source.

11. The apparatus or device of any of clauses 6-10, further comprising a prosthesis, wherein the second magnet module and the prosthesis are coupled together such that at least one of the position and orientation of the second magnet module relative to the first magnet module is dependent on at least one state of the prosthesis, thereby providing a tactile sensation indicative of the at least one state of the prosthesis.

12. The apparatus or device of any of clauses 1-10, further comprising a prosthesis, wherein the controller is configured to control the magnetic field applied to the first magnet module dependent on at least one state of the prosthesis, thereby providing a tactile sensation indicative of the at least one state of the prosthesis.

13. The apparatus or device of clause 11 or 12, wherein:
   the prosthesis comprises a prosthetic limb comprising a first component and a second component, wherein one or more of the following is changeable: a position of the first component relative to the second component, an orientation of the first component relative to the second component, and a shape of the first component; and
   the at least one state of the prosthesis comprises one or more of the following: the position of the first component relative to the second component, the orientation of the first component relative to the second component, and the shape of the first component.

14. The apparatus or device of any of clauses 11-13, wherein the at least one state of the prosthesis comprises a size and/or spatial distribution of a pressure applied to the prosthesis.

15. A method of providing tactile sensation, comprising:
   providing a first magnet module comprising one or more magnetic elements;
   controlling a tactile sensation applied by the first magnet module to a human or animal body to which the first magnet module is mounted by controlling a magnetic field applied to the first magnet module.

16. The method of clause 15, wherein the first magnet module to adhered to skin of the human or animal body.

17. A method of providing tactile sensation to a user of a control device via a gripping portion of the control device while the user is holding the gripping portion, wherein a first magnet module comprising one or more magnetic elements is provided and the method comprises controlling the tactile sensation applied by the first magnet module to the user through the gripping portion by controlling a magnetic field applied to the first magnet module.

18. The method of clause 17, wherein the gripping portion allows the user to move a first component of the control device relative to a second component of the control device to provide a control signal.

19. The method of any of clauses 15-18, wherein the tactile sensation is controlled in a continuously variable manner by applying a continuously variable control of a force distribution applied to the one or more magnetic elements.

20. The method of any of clauses 15-19, wherein the first magnet module comprises a plurality of magnetic elements mounted spaced apart from each other.

21. The method of any of clauses 15-20, wherein a second magnet module is provided and the controlling of the magnetic field applied to the first magnet module is implemented by controlling at least one of the position and orientation of the second magnet module relative to the first magnet module.

22. The method of clause 21, wherein movement of the second magnet module relative to the first magnet module is guided using a guide.

23. The method of clause 22, wherein the guide is fixedly mounted relative to the first magnet module.

24. The method of clause 23, wherein:
the guide allows movement of the first magnet module between a distal position and a proximal position;
the distal position is a position at which a magnetic interaction between the first magnet module and the second magnet module is too weak to cause a tactile sensation; and
the proximal position is a position at which the magnetic interaction between the first magnet module and the second magnet module is strong enough to cause a tactile sensation.

25. The method of any of clauses 15-24, wherein the magnetic field applied to the first magnet module is at least partially generated using an electrical power source.

26. The method of any of clauses 21-25, wherein the second magnet module and a prosthesis are coupled together such that at least one of the position and orientation of the second magnet module relative to the first magnet module is dependent on at least one state of the prosthesis, thereby providing a tactile sensation indicative of the at least one state of the prosthesis.

27. The method of any of clauses 15-26, further comprising controlling the magnetic field applied to the first magnet module dependent on at least one state of a prosthesis, thereby providing a tactile sensation indicative of the at least one state of the prosthesis.

28. The method of clause 26 or 27, wherein:
the prosthesis comprises a prosthetic limb comprising a first component and a second component, wherein one or more of the following is changeable: a position of the first component relative to the second component, an orientation of the first component relative to the second component, and a shape of the first component; and
the at least one state of the prosthesis comprises one or more of the following: the position of the first component relative to the second component, the orientation of the first component relative to the second component, and the shape of the first component.

29. The method of any of clauses 26-28, wherein the at least one state of the prosthesis comprises a size and/or spatial distribution of a pressure applied to the prosthesis.

The invention claimed is:

1. Apparatus for providing tactile sensation, comprising:
a first magnet module comprising one or more magnetic elements;
a mounting arrangement configured to mount the first magnet module to a human or animal body; and
a controller configured to control a tactile sensation applied by the first magnet module to the human or animal body by controlling a magnetic field applied to the first magnet module, wherein:
the one or more magnetic elements of the first magnet module are rotatably mounted and the controller is configured to control the applied tactile sensation by rotating one or more of the magnetic elements using the applied magnetic field;
the one or more magnetic elements are each cylindrically asymmetric about an axis of the rotation; and
the apparatus further comprises a second magnet module, wherein the controller is configured to control the magnetic field applied to the first magnet module by controlling at least one of the position and orientation of the second magnet module relative to the first magnet module.

2. The apparatus of claim 1, wherein an axis of rotation of each of the one or more magnetic elements is a fixed axis of rotation relative to the mounting arrangement.

3. The apparatus of claim 1, wherein the first magnet module comprises a plurality of magnetic elements mounted spaced apart from each other.

4. The apparatus of claim 3, wherein all of said plurality of magnetic elements are rotatably mounted so as to be rotatable about a common fixed axis of rotation.

5. The apparatus of claim 1, further comprising a guide for guiding movement of the second magnet module relative to the first magnet module.

6. The apparatus of claim 5, wherein the guide is fixedly mounted relative to the first magnet module.

7. The apparatus of claim 5, wherein:
the guide allows movement of the first magnet module between a distal position and a proximal position;
the distal position is a position at which a magnetic interaction between the first magnet module and the second magnet module is too weak to cause a tactile sensation; and
the proximal position is a position at which the magnetic interaction between the first magnet module and the second magnet module is strong enough to cause a tactile sensation.

8. The apparatus of claim 1, wherein the mounting arrangement holds the one or more magnetic elements of the first magnet module so as to apply a pressing force against a skin without adhesive.

9. A control device having a gripping portion configured to be held in use by a user of the control device while moving a first component of the control device relative to a second component of the control device to provide a control signal, wherein the control device comprises:
a first magnet module comprising one or more magnetic elements; and
a controller configured to control a tactile sensation applied by the first magnet module to the user through the gripping portion by controlling a magnetic field applied to the first magnet module, wherein:
the one or more magnetic elements of the first magnet module are rotatably mounted and the controller is configured to control the applied tactile sensation by rotating one or more of the magnetic elements using the applied magnetic field;
the one or more magnetic elements are each cylindrically asymmetric about an axis of the rotation; and the control device further comprises a second magnet module, wherein the controller is configured to control the magnetic field applied to the first magnet module by controlling at least one of the position and orientation of the second magnet module relative to the first magnet module.

\* \* \* \* \*